Figure 1:
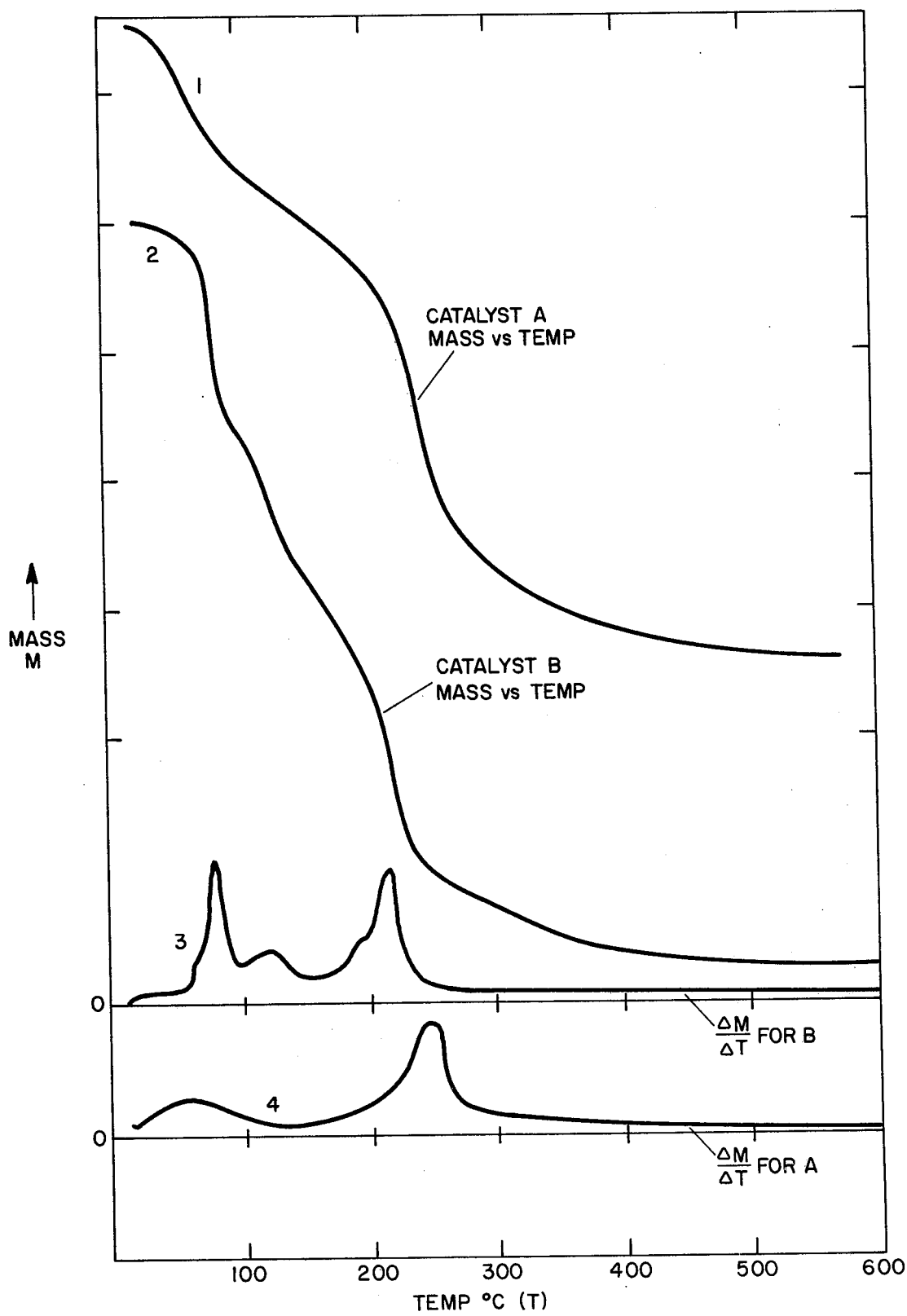

United States Patent [19]

Yates et al.

[11] 4,142,962
[45] Mar. 6, 1979

[54] HYDROGENATION AND HYDROCRACKING WITH HIGHLY DISPERSED SUPPORTED NICKEL CATALYSTS

[75] Inventors: David J. C. Yates, West Millington; Lawrence L. Murrell, Elizabeth, both of N.J.

[73] Assignee: Exxon Research & Engineering Co., Florham Park, N.J.

[21] Appl. No.: 877,505

[22] Filed: Feb. 13, 1978

Related U.S. Application Data

[63] Continuation-in-part of Ser. No. 688,154, May 20, 1976, Pat. No. 4,073,750.

[51] Int. Cl.$^2$ .................. C10G 13/02; C07C 5/10; B01J 27/04; B01J 35/10
[52] U.S. Cl. .................. 208/109; 208/112; 208/143; 252/459; 252/466 J; 252/477 R; 260/667; 260/676 R; 423/654
[58] Field of Search .................. 208/109–112; 260/667, 676 R; 252/459, 466 J, 472; 423/654

[56] References Cited

U.S. PATENT DOCUMENTS

| | | | |
|---|---|---|---|
| 3,536,632 | 10/1970 | Kroll | 208/109 |
| 3,692,701 | 9/1972 | Box | 252/455 B |
| 3,840,475 | 10/1974 | Davis | 252/441 |

Primary Examiner—Delbert E. Gantz
Assistant Examiner—G. E. Schmitkons

Attorney, Agent, or Firm—R. J. Baran; Joseph J. Allocca

[57] ABSTRACT

This invention relates to a method for making supported nickel catalysts which are characterized as having the nickel in a highly dispersed state, the catalysts and use thereof in hydrogenation, reforming and hydrocarbon synthesis reactions, for example, Fischer-Tropsch reactions. Catalysts prepared by the method of the instant invention, wherein nonaqueous solutions are used in preparing the catalyst, are characterized as having a degree of dispersion of at least 10% greater than similar catalysts prepared by the prior art aqueous impregnation techniques and in some instances show an improved degree of dispersion of more than 50% over the catalysts prepared by the prior art methods. In the method of the instant invention the catalyst is prepared by slurrying a nickel metal precursor dissolved in a nonaqueous organic solvent with a high surface area support, for example, a refractory inorganic oxide, preferably selected from the group consisting of silica and alumina, removing the solvent to obtain a composite of said nickel metal precursor and said support and activating said composite by reducing in hydrogen at conditions sufficient to convert substantially all the nickel metal precursor to nickel metal. The nonaqueous solvent is preferably selected from the group consisting of aldehydes, ketones, ethers and organic nitrogen compounds, for example, acetone, acetonitrile, N-N-dimethyl formamide, hexamethyl phosphoramide, diethylether, tetrahydrofuran, dioxane, methylethyl ketone and acetaldehyde.

18 Claims, 2 Drawing Figures

FIGURE I

HYDROGENATION AND HYDROCRACKING WITH HIGHLY DISPERSED SUPPORTED NICKEL CATALYSTS

CROSS REFERENCE TO RELATED APPLICATIONS

This application is a continuation-in-part of Ser. No. 688,154 filed May 20, 1976, now U.S. Pat. No. 4,073,750.

FIELD OF THE INVENTION

This invention relates to a method for making supported nickel caatalysts which are characterized as having the nickel in a highly dispersed state, the catalysts and use thereof in hydrogenation, reforming and hydrocarbon synthesis reactions, for example, Fischer-Tropsch reactions.

Further uses to which the catalysts prepared by the process disclosed in the instant application can be put include cracking, dehydrogenation, polymerization, isomerization, alkylation. These catalysts are also useful as scavengers of oxygen in inert gas purification processes and also as scavengers of sulfur compounds from various petrochemical streams. Catalysts prepared by the method of the instant invention, wherein nonaqueous solutions are used in preparing the catalyst, are characterized as having a degree of dispersion of at least 10% greater than similar catalysts prepared by the prior art aqueous impregnation techniques and in some instances show an improved degree of dispersion of more than 50% over the catalysts prepared by the prior art methods.

The catalyst of the instant invention is prepared by slurrying a nickel metal precursor dissolved in a nonaqueous organic solvent with a high surface area support, for example, a refractory inorganic oxide, preferably selected from the group consisting of silica and alumina, removing the solvent to obtain a composite of said nickel metal precursor and said support and activating said composite by reducing in hydrogen at conditions sufficient to convert substantially all the nickel metal precursor to nickel metal. The catalyst prepared by this method is a highly dispersed supported nickel catalyst having a nickel surface area of from 200 to 400 $m^2$/g nickel.

The nonaqueous solvent is preferably selected from the group consisting of aldehydes, ketones, ethers and organic nitrogen compounds, for example, acetone, acetonitrile, N-N-dimethyl formamide, hexamethyl phosphoramide, diethylether tetrahydrofuran, dioxane, methylethyl ketone and acetaldehyde.

DESCRIPTION OF THE PRIOR ART

Nickel catalysts, especially supported nickel catalysts, have many commercial uses, for example, U.S. Pat. No. 3,535,271 teaches the use of nickel catalysts promoted by copper for dehydrogenation. This patent also mentions that these catalysts can be used in cracking, reforming, polymerization, isomerization, alkylation, as well as other treating processes. Other examples of nickel catalysts and their use in various reforming, etc. processes include U.S. Pat. Nos. 3,205,182, 2,750,261 and 3,868,332. In all of these references, the catalysts are prepared by coprecipitation or impregnation processes wherein the catalytic metal precursors are either precipitated from solution in the presence of a support material or solutions containing said precursor are impregnated into the pores of a porous support material. In all of these references, however, the solutions utilized in the coprecipitation or impregnation processes are aqueous solutions. In the British Pat. No. 1,220,105, for example, aqueous solutions are employed in conjunction with a homogeneous precipitation procedure to give highly dispersed nickel catalysts. It should be pointed out that extremely long precipitation periods were employed to prepare catalysts in the above invention. Nowhere in this patent were nonaqueous solvents suggested as a means to prepare highly dispersed nickel catalysts, however.

In various other references the preparation of supported catalysts is taught and during the course of disclosing the preparation of said catalysts it is pointed out that aqueous or nonaqueous solutions could be used in preparing the catalyst. However, the actual preparations as exemplified by the working examples in all of these references show aqueous solutions being used in the preparation steps; see, for example, U.S. Pat. No. 3,759,825, U.S. Pat. No. 3,641,182 and U.S. Pat. No. 3,692,701.

U.S. Pat. No. 3,536,632 issued to W. R. Kroll teaches a catalyst prepared by use of a nonaqueous solution to deposit a metal compound on the support, but activates the catalyst with an organometallic reducing agent. Nowhere in this patent was it recognized that activation of the catalyst with hydrogen at elevated temperature could be effected and would give a more highly dispersed nickel catalyst.

In U.S. Pat. No. 3,553,102 a nonaqueous sulfur containing solvent was employed to prepare palladium on zeolite catalysts. The basis of this invention is the preferred formation of palladium sulfide within the pores of the zeolite catalyst. This patent is clearly distinguished from the use of nonaqueous solvent in the method of the instant invention in that essentially complete removal of the nonaqueous solvent is desirable. Furthermore, it is known that sulfur residues on a nickel containing catalyst would be highly detrimental to catalytic activity of nickel based catalysts.

British Pat. No. 1,306,158 teaches use of nonaqueous solutions for catalyst preparation of W, Mo, and Re catalysts on zeolite supports. This application of nonaqueous solutions employed alcohol solvents exclusively for the desired purpose of ion exchange incorporation of the W, Mo, and Re precursors into the zeolite catalyst. This patent is clearly distinguishable from the instant invention in that the purpose of utilizing nonaqueous solvents to deposit nickel catalyst precursors onto inorganic supports is to achieve high metal dispersion.

U.S. Pat. No. 3,840,475 employs nonaqueous solutions to prepare bimetallic catalysts for hydrocarbon conversion processes wherein the bimetallic catalysts are Pt—Sn, or Rh—Sn. Nowhere is it discussed that analogous aqueous preparations result in catalysts having an inferior degree of dispersion.

In U.S. Pat. No. 3,868,332, noted above, the patentees faced the problem of obtaining a high degree of dispersion of nickel metal on their support. The patentee appreciated the higher degree of dispersion would give more active catalysts and indeed obtained a fairly high degree of dispersion by their coprecipitation technique wherein nickel cations were precipitated from an aqueous solution in the presence of silicate anions. However, their degree of dispersion as calculated on the basis of nickel metal is taught to be greater than 140 $m^2$/g. The process of the instant invention, by use of a nonaqueous preparation technique as opposed to the aqueous preparation technique of U.S. Pat. No. 3,868,332 has been able to achieve dispersions of up to 400 m$^2$/g of nickel metal. Thus it is clear an improved degree of dispersion over the best prior art nickel catalysts has been achieved by means of the novel process of the instant invention.

SUMMARY OF THE INVENTION

It has now been unexpectedly discovered that a catalyst comprising nickel supported on a support material, wherein the nickel is characterized as having a high surface area, for example, an improvement in dispersion of at least 10%, more preferably at least 50% over similar catalysts prepared by the prior art aqueous impregnation and/or aqueous coprecipitation techniques, can be obtained by utilizing a nonaqueous solution in the preparation of the catalyst. In the method of the instant invention a nickel metal precursor dissolved in a nonaqueous solvent is slurried with a support material, for example, a refractory inorganic oxide, the solvent is removed to yield a composite of said nickel metal precursor and said support material and finally the composite is activated by reducing with hydrogen at conditions sufficient to convert substantially all of the nickel metal precursor to nickel metal. The nonaqueous organic liquid is conveniently selected from the group consisting of aldehydes, ketones, ethers and organic nitrogen compounds. More preferably the nonaqueous solvent is selected from the group consisting of acetone, acetonitrile, N,N-dimethyl formamide, diethylether, tetrahydrofuran, dioxane, methylethyl ketone, and acetaldehyde.

Preferably for commercial use in the preparation of the catalysts of the instant invention the solvent will be selected from the group consisting of volatile organic liquids, for example, materials having a boiling point of less than 100° C. are preferred for use in preparing the catalysts of the instant invention.

The nickel metal precursors will be selected from materials which are soluble in the above-described solvents. The nickel metal precursor should be chosen to have sufficient solubility so that one preparing the catalyst will not have to utilize large volumes of solvent. From a commercial standpoint recycling, that is the removing of the solvent and subsequent reuse, may be uneconomical when volumes of greater than 10 volumes of solvent per volume of support are used during the slurrying step. Thus it is important to choose nickel metal precursors having a high degree of solubility in the solvent used. Examples of soluble nickel metal precursors include both salts and organonickel compounds.

An example of organonickel compounds, includes, for example, nickel carbonyls, cyclopentadienyl nickel complexes, etc. Nickel salts which can be used as nickel metal precursors include nickel nitrate, nickel chloride, nickel carbonate, various nickel carboxylates such as the acetates, formates, propionates, etc. It is important when choosing the nickel metal precursor to avoid the use of materials containing sulfur, phosphorus, alkali metals such as sodium, potassium, lithium and alkaline earth metals, for example, calcium, barium, etc. These materials are known catalyst poisons and thus must be avoided in the preparation of the active catalysts of the instant invention.

In the most preferred embodiment of the instant invention the nickel metal precursor is nickel nitrate and the solvent is acetone. This embodiment is preferred due to the high volatility of acetone in combination with the high solubility of nickel nitrate therein. It is also important to note that the price of nickel nitrate is significantly less than the other above-mentioned nickel metal precursors.

The catalyst is prepared by slurrying the nickel metal precursor dissolved in a nonaqueous solvent with the support material and removing the solvent to obtain a composite of said support and said metal precursor. The slurrying and the removal of the solvent may be carried out serially, but in general these steps are done simultaneously. Where the conditions given below are given for the slurrying step, it is to be understood that solvent removal is also being effected.

In general the amount of solvent is greater than that necessary to fill the pores of the support material. This amount of solvent is necessary because the nickel loading of the catalysts of the invention, in general, varies from 2 to about 40 wt. % of total catalyst. At this loading the nonaqueous solvents will generally not dissolve enough nickel metal precursor to achieve this loading without the use of excess volumes. Multiple slurrying steps may be used to obtain high nickel loadings, if needed, but it is usually desired to achieve the composite described above during one slurrying operation.

This use of an excess volume of solvent may be contrasted to the prior art aqueous impregnation procedures wherein the volume of the aqueous solution may be approximately equal to the volume of the pores of the support.

During the slurrying step of the method of the instant invention, the conditions are adjusted so that the solvent is removed at a convenient rate. Thus it is commercially desirable to have a fairly high vapor pressure solvent. The temperature and pressure may be adjusted during the slurrying step to remove the solvent at a convenient rate, generally as fast as possible while maintaining fairly uniform contacting of the diminishing volume of solvent with the support. During the slurrying step agitation is provided to ensure intimate mixing of the solvent containing the dissolved nickel metal precursor and the support material.

The temperature during the slurrying step must be maintained high enough to ensure that the nickel metal precursor does not prematurely precipitate from solution. The solvent, as it vaporizes, lowers the temperature of the remaining liquid solvent, thus, it may be necessary to provide heating during the slurrying step in order to maintain the temperature high enough to provide rapid solvent removal without premature precipitation. Preferably the solvent temperature is maintained below the boiling point and for safety's sake it is generally desirable to maintain the solvent temperature below the flash point. In the most preferred method of carrying out the above slurrying step the solvent is maintained above the temperature at which precipitation of the nickel metal precursor occurs and below the boiling point while the pressure is kept at a level suitable to provide rapid evaporation. Alternatively, the solvent may be stripped by use of a purge gas, for example, dry gases such as nitrogen, argon, air, etc. may be used. In general a temperature of from about 20° C. to 90° C. may be utilized during the slurrying and the removing of the nonaqueous solvent. From room temperature, i.e. 25° C. to about 70° C. are preferred.

The slurrying operation can be carried out in equipment known in the art for removing large volumes of vapor. For example, the slurrying step may be carried out in a rotary evaporator which provides a convenient means of controlling the temperature, agitation rate and the rate at which the solvent is removed. Generally the slurrying step will be carried out for a time sufficient to ensure that substantially all of the solvent is removed although small amounts may be conveniently left. These small amounts of solvent will be removed during the subsequent activation step. In general the slurrying will take place for a time of from 10 to 1000 minutes, preferably 20 to 500 minutes, i.e. it generally takes about this much time to substantially remove the solvent.

After the above slurrying step a composite comprising the nickel metal precursor and the support material is recovered. This material is subsequently activated by reducing at a temperature and for a time sufficient to convert substantially all of the nickel metal precursor to nickel metal. The activation step is carried out by contacting the composite with a reducing gas comprising hydrogen. The reducing gas may be conveniently diluted with an inert gas such as nitrogen, etc. It is to be noted that for the purposes of this invention steam is not considered to be inert. The contacting of the catalysts prepared by the process of the instant invention with steam may adversely affect the degree of nickel metal dispersion. The temperatures at which the activation takes place are greater than 50° C. but lower than the temperature at which nickel metal dispersion is adversely affected, i.e. 450° C. Preferably the activation temperature is greater than 150° C., more preferably from 150° to 400° C.

The support material is selected from the group consisting of refractory inorganic oxides having a high surface area. For example, the surface area of the support material should be at least 10 m$^2$/g, preferably 100 to 300 m$^2$/g. The specific preferred examples of support material include silica, alumina, silica-alumina, magnesia, titania, zirconia, zirconium titanates, etc. More preferably the support is selected from the group consisting of silica and alumina. The most preferred support for use in preparing the catalysts of the instant invention is silica.

As alluded to above the catalysts will contain, after activation, from 2 to 40% by weight of nickel metal, more preferably 2 to 20% by weight nickel and even more preferably from 5 to 15% by weight nickel. The catalysts as noted above are characterized as having the nickel in a highly dispersed state. It will be appreciated by those skilled in the art and as discussed in detail in Example 1 that the more highly dispersed the nickel catalyst is the higher the activity obtained during use. In general the catalysts prepared by the method of the instant invention have a degree of dispersion at least 10% greater than a nickel catalyst prepared by the prior art aqueous techniques. More particularly it is possible by using the method of the instant invention to achieve a degree of dispersion greater than 50% of that achieved by the prior art processes. The catalysts of the instant invention can be prepared having a nickel surface area of from 200 to 400 m$^2$/g of nickel. This is a significant improvement over the prior art.

It is also to be noted that the catalysts prepared by the method of the instant invention wherein the nickel loading varies from about 10 to 20% show the most significant improvement in dispersion as compared with the prior art catalysts at similar nickel metal loadings. The loadings of from 10 to 20% nickel are significant from a commercial standpoint since it is necessary in most commercial operations to have a catalyst having at least about 10% by weight nickel metal, and in fact greater amounts of nickel loading are desired. Thus the instant invention provides a highly dispersed nickel at a loading level which is commercially significant.

The catalysts prepared by the method of the instant invention find their use in steam reforming processes, hydrocarbon synthesis, that is Fischer-Tropsch reactions, and hydrogenation. The catalysts prepared by the method of the instant invention are especially useful in hydrogenation reactions, that is the reduction of unsaturated bonds, such as carbon-carbon, carbon-nitrogen, carbon-oxygen, etc. bonds. For example, the hydrogenation of olefins, including diolefins, etc.; aromatics; aldehydes, both saturated and unsaturated prepared by the Oxo process; edible fats and oils and nitro compounds to obtain amines may be catalyzed by said catalysts. Preferably $C_2$ to $C_{20}$ olefins, including both straight and branched chain olefins, $C_6$ to $C_{20}$ aromatics including condensed nonaromatics and $C_1$ to $C_{20}$ aldehydes are hydrogenated with the catalysts prepared by the method of the instant invention. A particular hydrogenation process wherein the catalysts of the instant invention may be used is the conversion of benzene to cyclohexane.

The hydrogenation processes utilizing the catalysts prepared by the method of the instant invention are conveniently carried out at temperatures of from 25° C. to 250° C., preferably from 75° C. to 175° C., and at pressures of from atmospheric to 800 atm, preferably from atmospheric to 50 atm. Feed rates of from 0.2 to 100 volumes per hour per volume of catalyst and hydrogen addition of from 2,000 to 10,000 standard cubic feet per barrel of feed may be used.

The catalysts may also comprise promoter metals in addition to the active nickel metal, for example, copper, silver or gold. Palladium, or other Group VIII metals may be added to the catalyst at any point during its manufacture. Generally the promoter metal will be added during the slurrying step noted above. Thus materials that are soluble in organic solvents will be utilized as promoter metal precursors. For example, if copper is utilized as a promoter, copper nitrate, copper chloride, copper carbonate, etc. may be dissolved, in addition to the nickel metal precursor, in the nonaqueous solvent of choice. Typically the promoter will be added to the catalyst at a level of 1/10 or less, on a weight basis, than the level of the nickel metal.

The catalyst precursor, i.e. the composite of the support and the nickel metal precursor is also novel. As further described hereinbelow the composite, when prepared by the nonaqueous method of the instant invention behaves differently, upon decomposition in air or oxygen than a similar composite prepared by an aqueous method.

Figure 2:
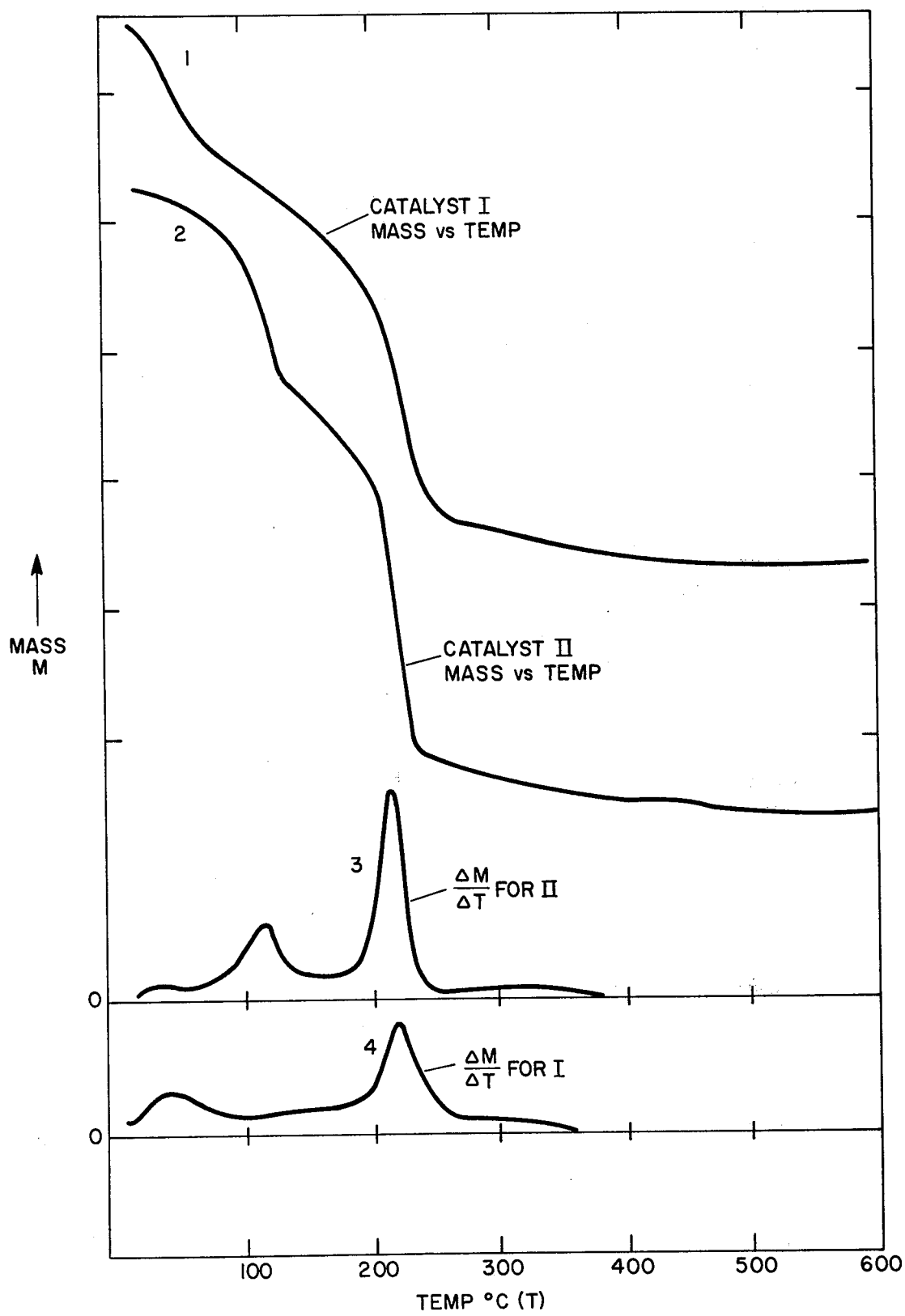

FIGS. 1 and 2 show this different decomposition behavior of catalyst precursors prepared by aqueous and nonaqueous methods.

The following are the preferred embodiments of the instant invention.

EXAMPLE 1

The main parameter which controls the activity of supported nickel catalysts, other physical factors (such as pore size) being equal, is the particle size of the nickel. For many systems this can be measured by X-ray diffraction line broadening. However, the more active a catalyst, the smaller the particle size of the nickel and active catalysts will often have particle sizes less than 50Å (i.e. $5 \times 10^{-7}$ cm). Unfortunately, the X-ray line broadening method is not applicable to particles smaller than 50Å. For such particles, the only two methods commonly used are electron microscopy and chemisorption. The former, while direct, only measures a few micrograms of the catalyst in one photograph and hence has very severe sampling problems if the catalyst is at all nonuniform in nickel distribution. The chemisorption method depends on measuring the gas uptake of a gas which is adsorbed only on the nickel and not on the support. Such a gas is hydrogen; it is dissociatively adsorbed on clean nickel surfaces at room temperature, and is not physically adsorbed on the support (as the boiling point of $H_2$ is 21° K.).

The whole chemisorption technique and its utility in correlating nickel particle size (and/or nickel surface area) with catalytic activity has been published in detail by one of the inventors of this application (D. J. C. Yates, W. F. Taylor and J. H. Sinfelt, J. Amer. Chem. Soc., 86, 2996 1964).

FIG. 3 in that publication shows that a direct relation exists between nickel area (as $m^2$/gm of catalyst) and initial reaction rate for ethane catalytically converted into methane (as mmoles $C_2H_6$ converted per hour per gm catalyst). It follows, then, that any method which improves the nickel area of a nickel catalyst (other factors such as nickel content remaining constant) is a desirable feature, leading to a catalyst of improved utility.

Such a method has been found, by the unexpected discovery that a nonaqueous preparation of nickel catalysts leads to a much improved nickel dispersion relative to the almost universal use of aqueous methods of preparation of nickel catalysts.

A catalyst was prepared under essentially anhydrous conditions by the use of a dry box, with a high area silica powder (Cabosil) available from G. Cabot Co. using very dry acetone as the solvent to dissolve the nickel nitrate. The acetone was then removed from the mixture by a vacuum at room temperature (Catalyst A). The amount of nickel nitrate and silica used was such that the catalyst contained 5 w. % Ni after reduction.

Using the same silica, a catalyst was prepared with the same nickel content by incipient wetness, with distilled water as the solvent. The excess water was removed by drying in air at 110° C. overnight. Complete details of the aqueous preparative technique can be found in the article previously referred to (JACS). A series of catalysts were prepared in a similar fashion, and Table I shows data obtained by hydrogen chemisorption on 10 catalysts, 5 prepared with anhydrous solvents and 5 prepared with water as the solvent for nickel nitrate.

The percentage nickel column refers to weight percentage nickel (as metallic nickel) after reduction of the catalyst. The supports used were both pure, for the silica a high purity product was used, and for the alumina a high purity gamma alumina was used similar to that commonly used in preparing platinum on alumina reforming catalysts. The reduction temperature refers to the highest temperature used in reduction; all reductions were carried out in pure flowing hydrogen.

The nickel area is expressed in two ways, as square meters per gram of catalyst ($\Sigma$) and as square meters per gram of nickel ($\Sigma_m$). The first way is directly related to the activity of the catalyst in a reactor which contains a given weight of catalyst; the second gives one basic information related to the nickel particle size. Assuming spherical particles, the nickel area per gram of nickel is related to the particle size (d) by the relation $\Sigma m = 6/l \cdot d$ where l is the density of nickel. Values of d in Å (1Å $= 10^{-8}$ cm) are given in the next to last column. If all the atoms of a given crystallite are in the surface, this is the maximum attainable dispersion. For nickel, this is 666 $m^2$/gm Ni. Hence by dividing $\Sigma m$ by 666, and expressing the answer in percent one can obtain a measure of the dispersion efficiency one has obtained. This ranges from a low of 17% for aqueous Catalyst F to a high of 35% for the nonaqueous Catalysts A and C.

It will be noted from Table I that in all cases the nonaqueous catalysts have superior nickel dispersions relative to the aqueous catalysts containing the equivalent amount of Ni, thus demonstrating over a range of nickel contents, and supports, the superiority of the instant invention over the prior art.

TABLE I

| Catalyst | % Ni (After Reduction) | Method of Preparation | Support | Reduction Temp. °C | $\Sigma Ni$ Area $m^2$/gm Catalyst | $\Sigma Ni$ Area $m^2$/gm Nickel | Ni Particle Size in Å($10^{-8}$cm) | Ni Dispersion in Percent |
|---|---|---|---|---|---|---|---|---|
| A | 5 | Nonaqueous | $SiO_2$ | 450 | 11.7 | 234 | 29 | 35 |
| B | 5 | Aqueous | $SiO_2$ | 350 | 6.4 | 128 | 53 | 19 |
| C | 9 | Nonaqueous | $SiO_2$ | 450 | 21.0 | 234 | 29 | 35 |
| D | 10 | Aqueous | $SiO_2$ | 450 | 17.3 | 173 | 39 | 26 |
| E | 17 | Nonaqueous | $SiO_2$ | 400 | 35.1 | 210 | 32 | 31.5 |
| F | 17 | Aqueous | $SiO_2$ | 450 | 18.9 | 112 | 60 | 17 |
| G | 9 | Nonaqueous | $Al_2O_3$ | 450 | 21.1 | 235 | 29 | 35 |
| H | 8.8 | Aqueous | $Al_2O_3$ | 450 | 17.3 | 197 | 34 | 29 |
| I | 17 | Nonaqueous | $Al_2O_3$ | 450 | 30.5 | 179 | 37 | 27 |
| J | 17 | Aqueous | $Al_2O_3$ | 450 | 20 | 118 | 57 | 18 |

EXAMPLE 2

In order to demonstrate the superiority of the catalysts prepared by the method of the instant invention comparative catalytic investigations of ethane hydrogenolysis were conducted under identical experimental conditions using the identical catalysts characterized in Table I of Example 1.

The apparatus, procedure and analysis of data are available in the literature (D. J. C. Yates, W. F. Taylor and J. H. Sinfelt, J. Amer. Chem. Soc., 86, 2996 1964) and this procedure was adhered to in these experiments.

The nonaqueous Catalyst C was reduced in situ in the catalysis apparatus (described in the reference) at 450° C., then cooled to 150° C. and the ethane flow started. Conversions to methane were measured over a range of temperatures from 183° to 218° C., the values of the % conversion to $CH_4$ being over a range from 0.25 to 5.78. A good straight line was obtained for % conversion versus temperature; the values are given in Table II. A short extrapolation of the data gives a conversion of 6.6% at 220° C.

TABLE II

THE EFFECT OF THE METHOD OF PREPARATION OF NICKEL CATALYSTS ON THEIR ACTIVITY FOR ETHANE HYDROGENOLYSIS

| Catalyst C 9% Ni on SiO$_2$ (Nonaqueous) | | Catalyst D 9% Ni on SiO$_2$ (Aqueous) | |
|---|---|---|---|
| °C | % Conversion | °C | % Conversion |
| 183 | 0.25 | 212 | 0.37 |
| 184 | 0.275 | 217 | 0.54 |
| 192 | 0.522 | 223 | 0.97 |
| 198 | 0.925 | 229 | 1.65 |
| 205 | 1.81 | 236 | 2.79 |
| 210 | 3.00 | 241 | 4.35 |
| 218 | 5.78 | 245 | 6.44 |

The aqueously prepared Catalyst D was reduced in the identical fashion. Conversions to methane were measured from 212° to 245° C., the corresponding conversions varying from 0.37% to 6.44%. Interpolation at 220° C. gave a conversion of 0.72%.

Hence, at 220° C. the anhydrously prepared Ni catalyst (C) is 9.17 times as active for the reaction H$_2$ + C$_2$H$_6$→2CH$_4$ than the catalyst prepared by conventional aqueous methods, showing the advantage of the instant invention in giving more active catalysts.

EXAMPLE 3

Another reaction of interest, which is typical of a whole range of hydrogenation reactions, is the hydrogenation of benzene.

Accordingly, the utility of the instant invention has been demonstrated by using the catalysts described above to hydrogenate benzene.

Catalyst C, comprising 9% Ni on silica prepared with a nonaqueous solvent under anhydrous conditions (weighing 0.253 gm) was charged to a metal reactor. After pressure testing with helium, hydrogen was passed over the catalyst and the temperature increased slowly to 450° C. After maintaining this temperature for 2 hours, the catalyst was cooled to 100° C. in flowing hydrogen (flow rate 1.23 liters/min). When the temperature was steady at 100° C., pure liquid benzene was fed in at 0.12 cm$^3$/min. A series of product analysis was made by gas chromatographic techniques, and an average conversion to cyclohexane of 30.2% was observed. The maximum conversion was 32.4%, the minimum was 27.1%.

Catalyst D, weighing 0.251 gm, was charged to the same reactor and the above procedure followed exactly. An average conversion at 100° C. of 19.2% was observed, with a maximum of 20.3% and a minimum of 18%.

Evidently on an equal weight basis, Catalyst C prepared by the method of the instant invention is 1.6 times as active as Catalyst D. This ratio is, of course, similar to that expected from the superior nickel dispersion of Catalyst C compared to D.

EXAMPLE 4

To show that the catalyst precursor, i.e. the nickel metal precursor and support composite prepared by the method of the instant invention is a new composition of matter the following thermogravimetric experiments were done to determine the decomposition of said catalyst precursor.

Catalyst A contained 17% Ni, 1.7% Cu on alumina, and was made from nickel nitrate and copper nitrate via conventional aqueous methods. The alumina was identical to that used in preparing the catalysts of Example 1. The final drying of the catalyst was in air at 120° C.

Catalyst B was prepared from the identical alumina and metal salts, but acetone was used as the solvent. The final removal of acetone was done in vacuum at about 40° C.

Catalyst A was loaded into a thermogravimetric (TGA) apparatus (Fischer TGA Series 100), which uses a Cahn microbalance to measure the weight changes. The weight of the catalyst charged to the microbalance was 40.89 milligrams (mg). Oxygen was passed over the catalyst at a flow rate of 200 cm$^3$/min, and the furnace round the sample heated at a constant rate of 2° C./min, up to a maximum temperature of 600° C. Line 1 in FIG. 1 shows the variation of mass with temperature of the sample; its final weight was 31.38 mg. To show the regions where the fastest changes in mass take place, the microbalance is fitted with the Cahn time derivative computer Mark II, which gives the slope of the mass vs temperature curve, or $\Delta M/\Delta T$. This plot for Catalyst A is shown at the bottom of the Figure (line 4). It will be seen that only two peaks occur in the $\Delta M/\Delta T$ curve for Catalyst A; at 55° and 245° C. The peak at 55° C. is probably due to water desorption from the sample, the water being absorbed on the alumina while transferring it from the drying oven to the microbalance. Heating sample A in a test tube in a furnace at 110° C. while observing the gases given off visually showed no nitric oxides (NO$_x$) being formed, also confirmed via smell. The peak at 245° C. is, however, associated with the formation of NO$_x$ during the decomposition of the nickel nitrate, as shown in similar experiments in a test tube at higher temperatures.

Using identical experimental conditions, 36.01 mg of Catalyst B was changed to the TGA apparatus and heated in flowing oxygen to 600° C. The final weight of the sample was 25.16 mg. The general shape of the mass versus temperature curve for B (line 2) is different from A, but the differential curve for B shows how extremely large the differences are (line 3). In contrast with the two decomposition maxima with A, B shows four peaks, at 80°, 130°, 195° and 220° C. In a separate experiment, on heating Catalyst B in an air oven in a test tube at 100° C. copious evolution of NO$_x$ was noted hence the peak at 80° C. with Catalyst B is due to NO$_x$ formed during decomposition of the nickel nitrate, rather than adsorbed water. The other three peaks are also associated with NO$_x$ evolution.

Evidently, and unexpectedly to one familiar with the catalyst art, the decomposition temperatures of nickel nitrate deposited on a catalyst via anhydrous conditions are completely different from the thermal decomposition of nickel nitrate deposited via the conventional aqueous method on the same catalyst support. This difference shows directly that a new composition of matter occurs as a result of using the instant method of catalyst preparation.

EXAMPLE 5

To show that the new composition of matter is independent of the particular support, the following experiments were performed as in Example 4, but the supports used were changed from the alumina used in Example 4 to silica in the present example.

Catalyst I contained 17% nickel on silica (the same silica used in Example 1), and was prepared by conventional aqueous methods, using nickel nitrate as the salt. The final drying of the catalyst was in air at 120° C.

Catalyst II was prepared from the identical silica and nickel salt, but acetone was used as the solvent. The final removal of acetone was done in vacuum at about 40° C.

Catalyst I was loaded into the same thermogravimetric (TGA) apparatus as used in Example 4. The catalyst weighed 34.32 milligrams (mg) on charging to the microbalance, and was heated in flowing oxygen (200 cm$^3$/min) to 600° C. (heating rate 2° C./min) in the identical fashion to the procedure followed in Example 4. The final weight of the sample was 25.94 mg. Line 1 of FIG. 2 shows the variation of mass with temperature, line 4 of the same figure shows the differential of line 1 ($\Delta M/\Delta T$). It will be seen that only two peaks occur in the $\Delta M/\Delta T$ curve for Catalyst I (line 4, FIG. 2) at 40° and 220° C. (These are quite similar to the two peaks in the corresponding aqueously prepared sample in the previous example, line 4, FIG. 1, 55° and 245° C.) In a similar fashion to that discussed in detail in Example 4, the peak at 40° C. is considered to be associated with water desorbing from the sample, while that at 220° C. is due to the thermal decomposition of the nickel nitrate precursor into $NO_x$ and nickel oxide. Furthermore, heating the sample in air in a test tube in a furnace at 110° C. led to no $NO_x$ evolution, as determined by sight and smell.

Using identical experimental conditions and procedures, 34.2 mg of Catalyst II was changed to the TGA apparatus and heated in flowing oxygen to 600° C. The final weight of the sample was 24.41 mg. The decomposition curve for Catalyst II (line 3, FIG. 2) also shows two peaks, but they are at 120° and 220° C. In a separate experiment, on heating Catalyst II in an air oven at 120° C., brown fumes of $NO_x$ were noted, which composition was also confirmed by the smell of the gases coming off the catalyst. Heating the furnace to higher temperatures also showed that the 220° C. peak is associated with $NO_x$ evolution. It should be stressed that no evidence of a peak occurs with the aqueous catalyst (I) at 120° C., in fact, at that temperature there is a minima in the $\Delta M/\Delta T$ curve (compare lines 3 and 4 of FIG. 2).

These experiments show conclusively that the decomposition temperature of nickel nitrate on Catalyst I (made by conventional aqueous procedures) and Catalyst II (made using nonaqueous methods) are very different. This is entirely unexpected to anyone familiar with the prior art of catalyst preparation, and shows directly that a new composition of matter occurs as a result of using the instant method of catalyst preparation. Furthermore, this new composition of matter found by the use of nonaqueous methods is independent of the support used to prepare the nickel precursor (alumina in Example 4, silica in Example 5), and is therefore of general significance and importance.

What is claimed is:

1. In catalytic hydrogenation wherein the feedstream to be processed is contacted with a catalyst under hydrogenation reaction conditions, the improvement comprising using as the catalyst, a highly dispersed nickel catalyst having a nickel surface area of from 200 to 400 m$^2$/gram prepared by the method which comprises slurrying a nickel metal precursor dissolved in a nonaqueous organic liquid solvent with a high surface area refractory oxide support, removing the solvent to obtain a composite of said nickel metal precursor and said support, and activating said composite by reducing in hydrogen or hydrogen diluted with an inert gas at conditions sufficient to convert substantially all of the nickel metal precursor to nickel metal.

2. The process of claim 1 wherein the nonaqueous organic liquid used in the preparation of the catalyst is selected from the group consisting of aldehydes, ketones, ethers and organic nitrogen compounds.

3. The process of claim 1 wherein the support is selected from the group consisting of silica and alumina.

4. The process of claim 1 wherein the support is silica.

5. The process of claim 1 wherein the nonaqueous organic liquid used in the preparation of the catalyst is selected from the group consisting of acetone, acetonitrile, N,N-dimethyl formamide, hexamethyl phosphoramide, diethylether, tetrahydrofuran, dioxane, methylethyl ketone, and acetaldehyde.

6. The process of claim 1 wherein the nonaqueous organic liquid used in the preparation of the catalyst is acetone.

7. The process of claim 6 wherein the nickel metal precursor is nickel nitrate.

8. The process of claim 1 wherein the catalyst used comprises from about 2 to about 20 wt. percent nickel metal.

9. The process of claim 1 wherein the catalyst used is reduced in hydrogen or hydrogen diluted with an inert gas at a temperature of at least 150° C.

10. In catalytic hydrocracking processes wherein the feedstream to be processed is contacted with a catalyst under hydrocracking reaction conditions, the improvement comprising using as the catalyst a highly dispersed nickel catalyst having a nickel surface area of from 200 to 400 m$^2$/gram prepared by the method which comprises slurrying a nickel metal precursor dissolved in a nonaqueous organic liquid solvent with a high surface area refractory oxide support, removing the solvent to obtain a composite of said nickel metal precursor and said support, and activating said composite by reducing in hydrogen or hydrogen diluted with an inert gas at conditions sufficient to convert substantially all of the nickel metal precursor to nickel metal.

11. The process of claim 10 wherein the nonaqueous organic liquid used in the preparation of the catalyst is selected from the group consisting of aldehydes, ketones, ethers and organic nitrogen compounds.

12. The process of claim 10 wherein the support is selected from the group consisting of silica and alumina.

13. The process of claim 10 wherein the support is silica.

14. The process of claim 10 wherein the nonaqueous organic liquid used in the preparation of the catalyst is selected from the group consisting of acetone, acetonitrile, N,N-dimethyl formamide, hexamethyl phosphoramide, diethylether, tetrahydrofuran, dioxane, methylethyl ketone, and acetaldehyde.

15. The process of claim 10 wherein the nonaqueous organic liquid used in the preparation of the catalyst is acetone.

16. The process of claim 15 wherein the nickel metal precursor is nickel nitrate.

17. The process of claim 10 wherein the catalyst used comprises from about 2 to about 20 wt. percent nickel metal.

18. The process of claim 10 wherein the catalyst used is reduced in hydrogen or hydrogen diluted with an inert gas at a temperature of at least 150° C.

* * * * *